United States Patent [19]
Foley-Nolan et al.

[11] Patent Number: 5,478,303
[45] Date of Patent: Dec. 26, 1995

[54] ELECTROMAGNETIC APPARATUS FOR USE IN THERAPY

[76] Inventors: Darragh Foley-Nolan, 40 Kingswood Crescent, Roundhay, Leeds LS8 2BG, England; Frederick N. Hill, 2 Royal Canal Bank, Broadstone, Dublin 7, Ireland

[21] Appl. No.: 947,782

[22] Filed: Sep. 18, 1992

[51] Int. Cl.⁶ ................................................. A61N 1/00
[52] U.S. Cl. ................................................................ 600/15
[58] Field of Search ............................................ 600/9–15

[56] References Cited

U.S. PATENT DOCUMENTS

| | | | |
|---|---|---|---|
| 4,850,959 | 7/1989 | Findl | 600/14 |
| 5,195,941 | 3/1993 | Erickson et al. | 600/15 |

FOREIGN PATENT DOCUMENTS

| | | | |
|---|---|---|---|
| 0011019 | 5/1980 | European Pat. Off. | 600/13 |
| 1595121 | 1/1978 | United Kingdom . | |
| 2027594 | 2/1980 | United Kingdom . | |
| 2106394 | 4/1983 | United Kingdom . | |
| 2205754 | 6/1987 | United Kingdom . | |
| 0239098 | 9/1987 | United Kingdom . | |

OTHER PUBLICATIONS

"Low Energy High Frequency Pulsed Electromagnetic Therapy For Acute Whiplash Injuries", Scand. J. Rehab. Med. 24:51–59, 1992.

"Pulsed High Frequency (27MHz) Electromagnetic Therapy for Persistent Neck Pain A Double Blind, Placebo–Controlled Study of 20 Patients", published by Mater Misericordiae Hospital, Dublin, Ireland, Apr. 1990 In Orthopedics, vol. 13, No. 4.

English translation of Granted European Specification of European 02 39 098.

*Primary Examiner*—William E. Kamm
*Assistant Examiner*—John P. Lacyk
*Attorney, Agent, or Firm*—Felfe & Lynch

[57] ABSTRACT

A device for the controlled emission of electromagnetic radiation for use in medical and surgical conditions in humans and animals comprises a substrate which can be contoured to and placed in intimate contact with an area of the body of the human or animal to be treated, an electrical circuit integral with the substrate, including at least one inductance coil, and flexible with the substrate, and a power supply connected to the circuit. The electromagnetic radiation emitted by the device may be pulsed or continuous. The device has application in the alleviation of acute and chronic pain and in modulating cellular replication.

29 Claims, 3 Drawing Sheets

ELECTROMAGNETIC APPARATUS FOR USE IN THERAPY

FIELD OF THE INVENTION

This invention relates to a device for the controlled emission of electromagnetic radiation for use in medical and surgical conditions in humans and animals. Applications of the device include alleviation of acute and chronic pain and the modulation of cell replication, including the inhibition of malignant cell proliferation.

BACKGROUND AND PRIOR ART

Shortwave diathermy has been used over the last thirty years to stimulate tissue healing, especially in cases where conventional therapy is ineffective. Low frequency, medium power pulsed electromagnetic therapy (PEMT) devices have been used for example to accelerate fracture healing in refractory cases. Higher frequency PEMT devices have been used to accelerate inter alia wound healing. Conventional PEMT treatment regimens generally require mains operated power supplies. More recently battery powered devices have been used. However, irrespective of the power supply used in such devices electromagnetic pulse generation occurs at a site remote from the treatment site. In the case of a battery operated device the oscillator circuit is housed in the battery 'box'. Such an arrangement has the disadvantages of high electrical losses, instability of resonating frequency and a limitation to a relatively narrow frequency range.

Direct current fields administered by implanted electrodes have been used in the treatment of breast and lung tumours in the last ten years. Experimental work has been reported indicating an inhibition of ascites tumour cell growth exposed to permanent magnets of high field strength (of the order of 4,000 gauss). However, there have been no reports of the use of pulsed high frequency electromagnetic fields in the inhibition of tumour growth.

It is an object of the present invention to provide an improved electromagnetic therapy (EMT) device which overcomes the aforementioned disadvantages of conventional electromagnetic therapy devices and which by virtue of its structure and mode of operation can be used in a wide variety of therapeutic applications.

SUMMARY OF THE INVENTION

The invention provides a device for the controlled emission of electromagnetic radiation for use in medical and surgical conditions in humans and animals, which device comprises:

a substrate which can be contoured to and placed in intimate contact with an area of the body of said human or animal to be treated;

an electrical circuit which is integral and flexible with said substrate;

said electrical circuit including at least one inductance coil; and a power supply connected to said circuit, such that the generation of electromagnetic radiation occurs at the site of application of the device.

The device according to the invention has the advantages inter alia of achieving low losses of electromagnetic radiation, stability of resonating frequency and a variable frequency range.

The fact that the generation of electromagnetic radiation occurs at the site of application of the device means that loss of electromagnetic radiation at the site of application is minimal.

DETAILED DESCRIPTION OF PREFERRED EMBODIMENTS

Figure 1:
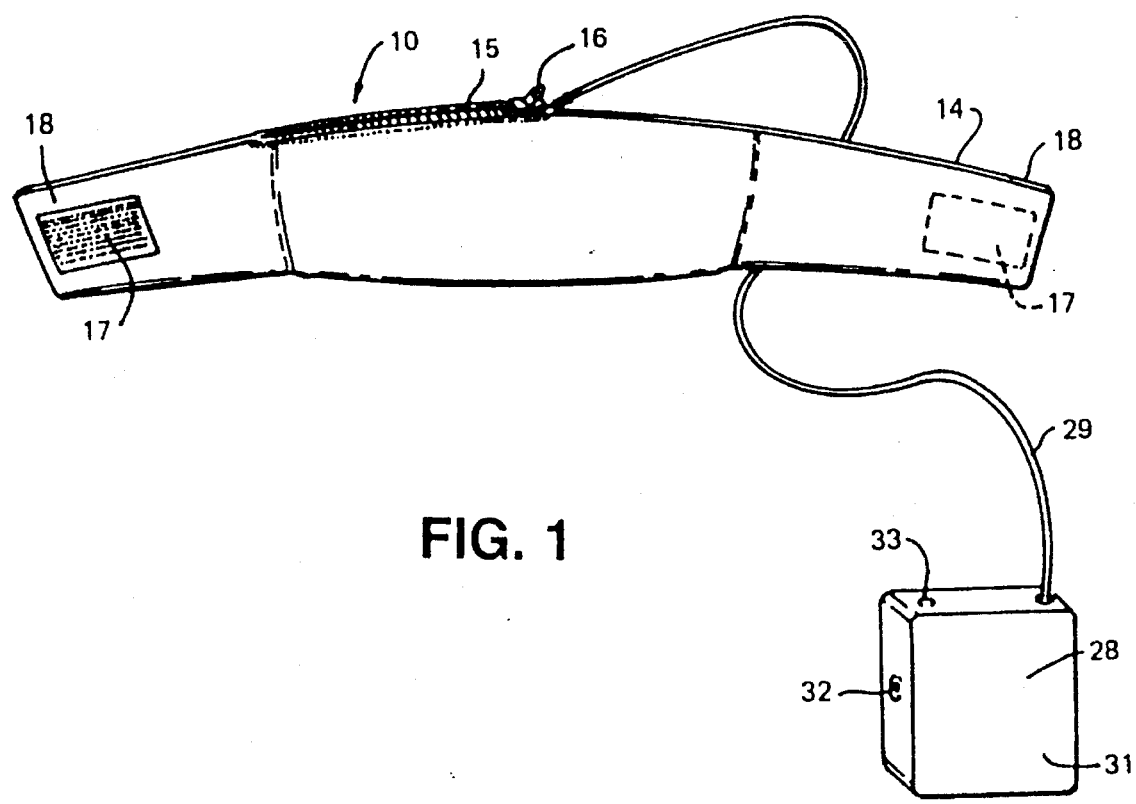
FIG. 1 is a perspective view of a device according to the invention.

The electromagnetic radiation emitted by the device may be pulsed or continuous. The electromagnetic radiation is preferably pulsed and the electrical circuit includes a pulse generating circuit and a pulse shaping network.

The electromagnetic radiation emitted by the device in accordance with the invention may be of a single waveform. In certain applications, such as the inhibition of malignant cell growth described below, the waveform is suitably sinusoidal. Alternatively, the electromagnetic radiation emitted by the device comprises a plurality of waveforms. Preferably, the waveform will have a rapid rise time viz a rapid change in amplitude per unit time.

The basic waveform produced by the device may be shaped to produce harmonics thereof. The electromagnetic radiation produced by the device may have a nominal frequency in the range 17–140 MHz.

Preferably, the electromagnetic radiation produced by the device has a nominal frequency in the range 20–30 MHz, more especially of the order of 27 MHz.

The device according to the invention suitably generates mean power in the range 1 to 3 milliwatts per $cm^2$, more especially 1.5 milliwatts per $cm^2$, at the surface of the area of the body to be treated.

Operating at low voltage there is no risk of electric shock or treatment hazard and no side effects have been observed in clinical trials involving prolonged application of the device.

The device according to the invention may include a microprocessor unit for generating electromagnetic radiation of variable frequency and waveform, for example, the device could be used to generate a specific pattern of alternating frequencies depending on the particular application of the device.

In a preferred embodiment the device includes a pair of flat rectangular helical inductance coils.

The substrate is preferably affixed to a pad of a cushioning material and housed in a sleeve of a suitable fabric for ready application to the body of a human or animal to be treated.

The power supply for the device suitably consists of one or more batteries. The power supply may consist of one or more 9 volt batteries located in a housing remote from the substrate and connected thereto by a lead. However, the power supply may also be integral with said substrate.

The device according to the invention can be used for the relief or treatment of various conditions such as: the treatment of pain in arthritis and rheumatism, sprains and the like lesions, dysmenorrhea and the alleviation of post-operative pain; and to accelerate wound healing of soft tissue injuries, post-operative surgical conditions and varicose ulcers.

The principle upon which wound healing therapy is based is the use of low energy, high frequency electromagnetic fields circulating within the area of tissue under treatment to effect cellular repair.

The materials used in the manufacture of the substrate and any components used to encapsulate or cover the substrate are such that the substrate may be sterilized where the use requires such sterilization, for example in post-operative analgesia and wound healing.

The substrate may be incorporated into a plaster cast, if required.

The device according to the invention has been designed primarily for use in home healthcare and is recommended for application by patients as an adjunct to treatment in the hospital or the physiotherapy department and in all cases where a definite medical diagnosis of a particular condition has been made.

In use the device according to the invention is secured over the affected area suitably whilst the subject being treated is resting or sleeping.

Thus the device according to the invention may be incorporated in a cervical collar for use in the treatment of acute or chronic neck pain. Such a cervical collar is especially useful for the treatment and alleviation of symptoms in symtomatic cervical spondylosis, whiplash injuries and persistent neck pain. For use in such conditions the pulse burst width generated by the device is preferably of the order of 50–70 μsec., especially 60 μsec. A device according to the invention for use in the treatment of acute or chronic neck pain would preferably emit pulsed electromagnetic radiation with a repetition frequency of the order of 400–500 cycles per second, more especially 450 cycles per second.

The device according to the invention has also been found to have application in the modulation of cell replication including the inhibition of cell proliferation, especially in the inhibition of malignant tumours. However, the device according to the invention can also be used to stimulate the replication of normal cells. Thus the device according to the invention has been found to stimulate the uptake of radioactive thymidine up to five times in corneal fibroblasts relative to controls. Thus a use for the device in the therapy of corneal transplants is postulated.

A device according to the invention for use in the inhibition of malignant tumours suitably emits electromagnetic radiation with a pulse burst width of the order of 250–350 μsec., more especially 300 μsec. Furthermore, the electromagnetic radiation emitted by the device in such applications suitably has a repetition frequency of the order of 200–400 cycles per second, more especially 333 cycles per second.

A device according to the invention for use in stimulating the replication of normal cells, for example corneal fibroblasts, suitably emits electromagnetic radiation with a pulse burst width of the order of 50–150 μsec., more especially 100 μsec. Furthermore, the electromagnetic radiation emitted by the device in such applications suitably has a repetition frequency of the order of 300–500 cycles per second, more especially 390 cycles per second.

Furthermore, the device according to the invention can be used for simultaneous, separate or sequential use with a chemotherapeutic agent in the treatment of malignancies. Preferably the chemotherapeutic agent is a metallo-organic compound, especially a platinum compound. The chemotherapeutic agent is suitably cisplatin ((SP-4-2)-diamminedichloroplatinum).

Referring now to the drawings wherein similar numerals have been used to indicate like pans, there is shown therein a device according to the invention, indicated generally at 10, in the form of a cervical collar. The device 10 comprises a substrate 11 (FIGS. 3a and 3b), to be described below, which is positioned between a sheet 12 of cushioning material and an elongate flexible backing element 13 which is of a shape similar to that of a fabric sleeve 14. The sleeve 14 has an opening 15 closable by means of a zip fastener 16 once the combined substrate 11, backing element 13 and sheet 12 are located in the sleeve 14. The backing element 13, sheet 12 and substrate 11 are affixed together by means of adhesive. The sleeve 14 also has complementary VELCRO (VELCRO is a Trade Mark) strips 17 adjacent the ends 18 thereof to secure the collar around a patient's neck.

Figure 3A:
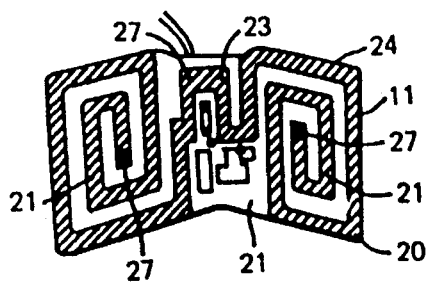
FIGS. 3a and 3b are front and rear views, respectively of the substrate which forms pan of the device of FIG. 1.
Figure 3B:
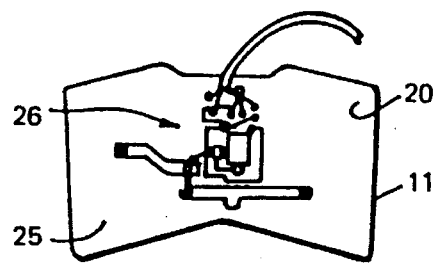
Figure 4:
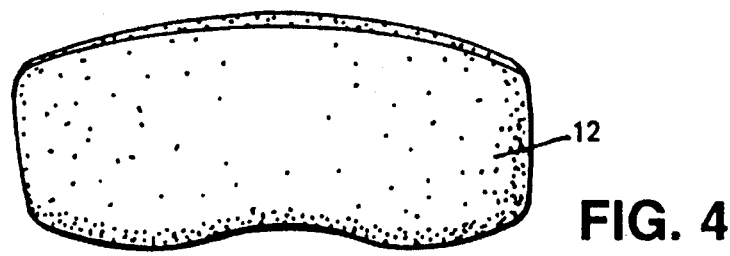
FIG. 4 is a front view of a sheet of cushioning material to which the substrate is affixed.
Figure 5:
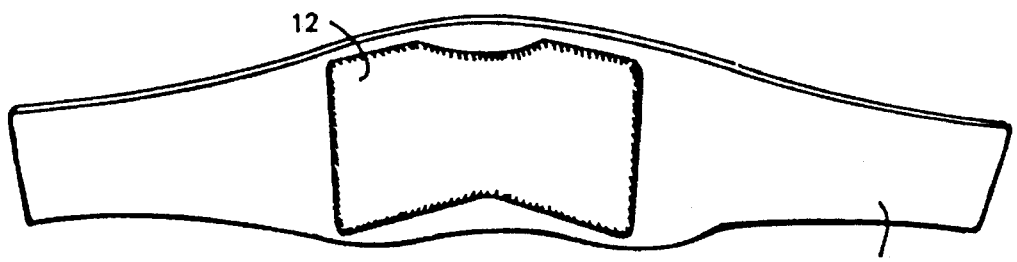
FIG. 5 is a front view of the substrate and the sheet of cushioning material affixed to a backing element.
Figure 6:
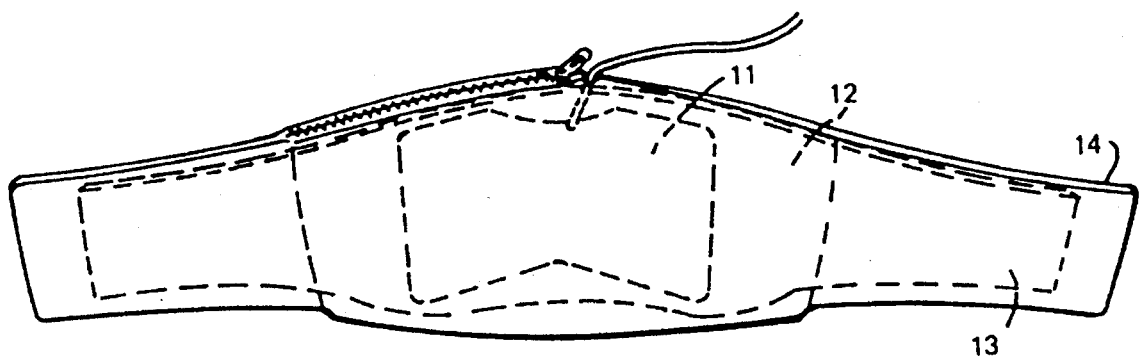
FIG. 6 is a front view of the device of FIG. 1 showing the various parts in dotted outline.

As shown in FIGS. 3a and 3b the substrate 11 comprises a flexible basal member 20 having a pair of flat rectangular helical inductance coils in the form of copper tracks 21 printed on one surface 22 thereof. The copper tracks 21 have a common connection 23 in the middle part of the substrate 11 adjacent the top edge 24. The other surface 25 of the member 20 has affixed thereon an electrical circuit 26 for energising the coils 21. The electrical circuit 26 is connected to the coils 21 by suitable connections 27 which extend through the member 20. The electrical circuit 26 is connected to a remote power supply 28 by a cable 29. The power supply 28 comprises two 9 volt batteries 30 located in a housing 31 which incorporates an on/off switch 32 and a light emitting diode 33 which indicates when the device is energised.

Figure 7:
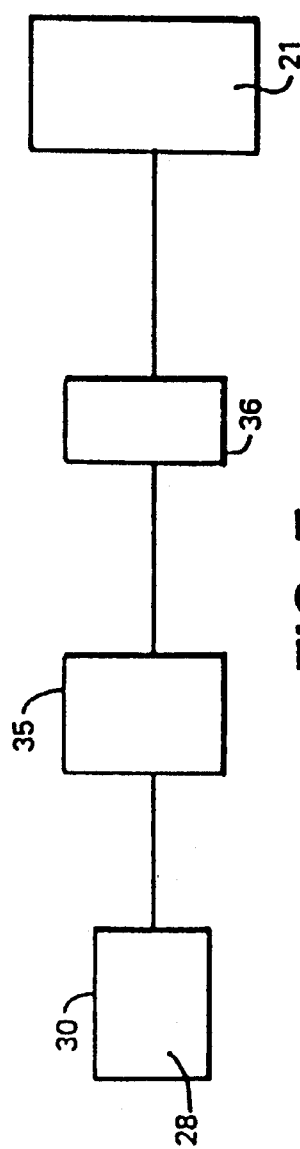
FIG. 7 is a block diagram of one circuit used in the device.

The electrical circuit 26 which is shown in block diagram form in FIG. 7 basically comprises the power supply 28, a pulse generating circuit and a filter 35, a pulse shaping network 36 and the coils 21.

Figure 8:
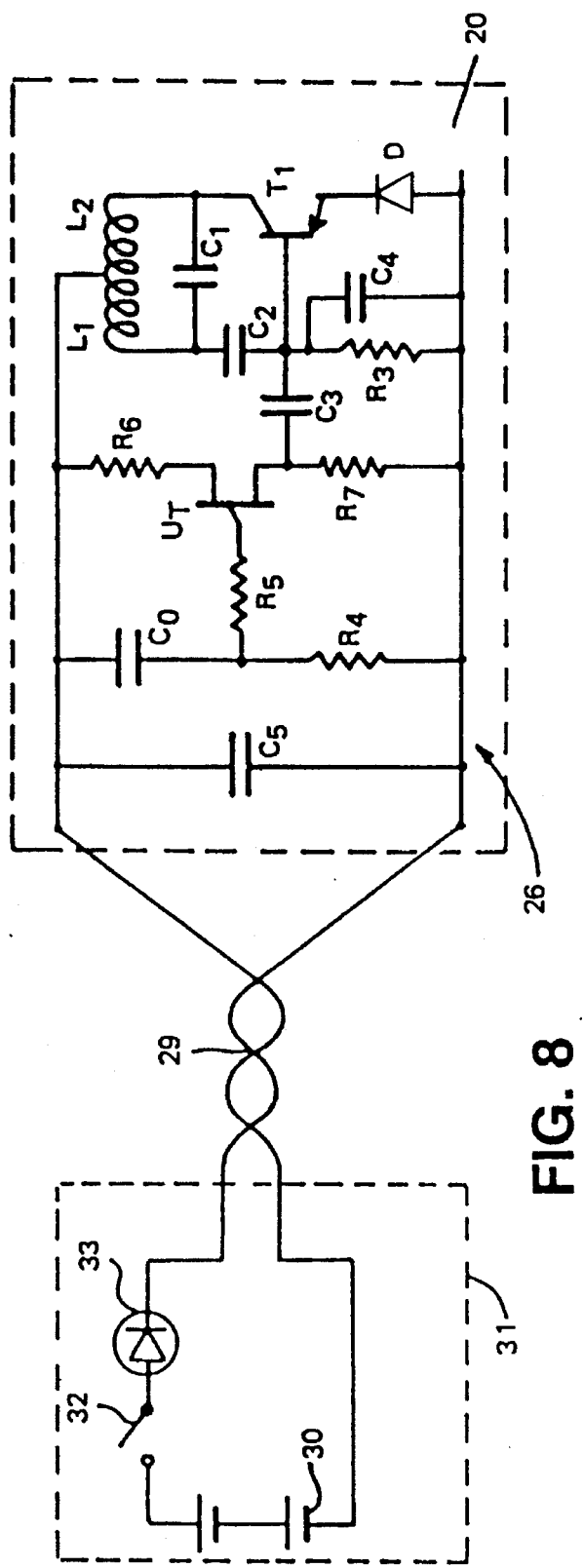
FIG. 8 is a more detailed circuit diagram of a circuit used in the device.

Referring now to FIG. 8, the electrical circuit 26 comprises an oscillator circuit including coils L1, L2 (i.e. the copper tracks 21 previously described), a capacitor C1 which is connected across the coils L1, L2 and a feedback capacitor C2. A transistor T1 derives its base supply from a pulse generated across the unijunction transistor UT. The pulse generated by the unijunction transistor UT is transferred to a coupling capacitor C3 and shaped by a resistor capacitor network R3, C4. The pulse duration and repetition frequency are determined by the timing capacitor Co and the resistor network R4, R5, R6, R7. A diode D is provided in the circuit to provide rapid turn off. Also provided in the circuit is a reservoir capacitor C5. The circuit is preferably arranged to produce a sinusoidal pulsed magnetic field in the area to be treated and having a mean power of 1.5 milliwatts/$cm^2$ at the surface of the neck of a patient to which the device is applied.

In an alternative embodiment the unijunction transistor and its circuitry may be replaced by a microchip to provide a more flexible waveform generation.

Figure 2:
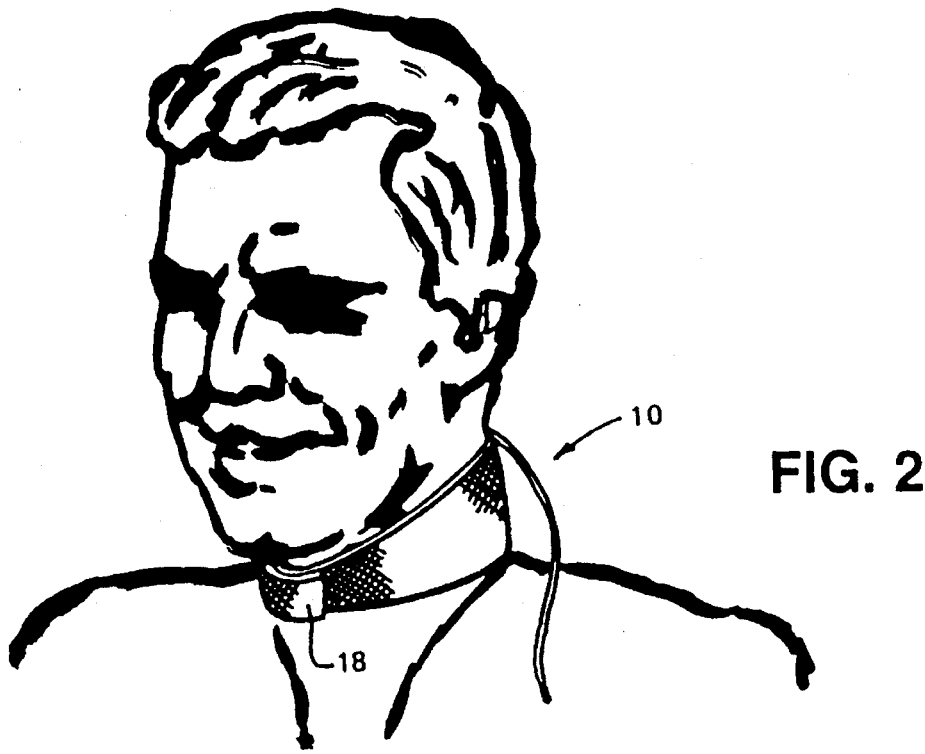
FIG. 2 is a perspective view of the device of FIG. 1 in use on a patient's neck.

In use the collar is secured around a patient's neck as shown in FIG. 2. The circuit 26 is energised by operating the switch 32. The housing 31 can be readily stored in for example a patient's shirt pocket. The surface 22 of the substrate 11 in use is nearest to the patient's neck. The low energy, high frequency magnetic fields produced by the device enable it to be safely used over long periods of time, if necessary. The device 10 has been found to produce minimal, if any, sensory stimulation. Furthermore, there is minimal, if any, generation of heat by the device.

CLINICAL TRIALS

Study 1

In the majority of patients with neck pain, symptoms resolve quite quickly in response to therapy or, indeed, spontaneously. However, the symptoms of some patients persist for a long period irrespective of therapy. In this study 20 patients with persistent (greater than eight weeks) neck pain were enrolled in a double blind placebo controlled six-week trial of low energy pulsed electromagnetic therapy (PEMT) at a frequency of 27 MHz, using the device according to the invention in the form of a cervical collar as described and as illustrated in the accompanying drawings. For the first three week period Group A (10 patients) received active PEMT using the device according to the invention, while Group B (10 patients) received facsimile placebo units. After three weeks both pain (visual analogue scale $p<0.023$) and range of movement ($p<0.002$) had improved in the group on active treatment compared to the controls. After the second three weeks, during which both groups used active units, there were significant improvements in observed scores for pain and range of movement in both groups.

Study 2

To assess the effect of treatment with PEMT in acute whiplash injuries a double blind randomised controlled trial of 40 patients, presenting within 72 h. of a rear impact road traffic accident, was undertaken: All patients received soft collars: half of these (20, Group A') had a device according to the invention (as in the case of Group A patients in Study 1) incorporated therein and half (20, Group B') had facsimile (placebo) units. The collars were worn for at least 8 h. daily. Patients were assessed on entry and at 2, 4 and 12 weeks. At 4 weeks if satisfactory progress had not been made the patients were referred for physiotherapy. Each assessment included the recording of pain, range of movement and a subjective assessment. A significant improvement ($p<0.05$) in pain was observed at 2 and 4 weeks in Group A' compared to Group B', while at 12 weeks there was no significant difference. While by chance, alone the movement scores of Group A' were significantly worse at entry to the study they were significantly better at 3 months ($p<0.05$).

The device according to the invention is easy to use and thus can be safely used in the home environment without the supervision of medically qualified personnel. Study 2 suggests that PEMT using the device according to the invention is of benefit to patients in the early management of acute whiplash injuries.

The advantages of the device according to the invention described with reference to the drawings include greater portability since all of the components are located in the sleeve 14 except for the power supply. A minimal number of circuit components are required and there is a stabilisation of the resonating frequency coupled with the use of a wide frequency range. The fact that the device can be contoured to and placed in intimate contact with the body enables the production of a uniform field of flux within the area to be treated.

Although the embodiment of the invention described above relates to the treatment of neck pain, at a particular energy level it will be appreciated that the device has application in treating other parts of the body at different energy levels, if desired. Furthermore, the incorporation of the coil(s) onto a flexible substrate enables the treatment coils to be contoured to any particular shape which is required.

Study 3

A study was carried out to examine the impact on cell growth of two small cell lung carcinoma lines H146 and H249 incubated for 96 h. with continuous exposure to a low energy 27 MHz pulsed electromagnetic field. $1 \times 10^5$ cells were plated in each case in multiple 96 well plates and an equal number of controls set up in parallel in 10% foetal calf serum and RPM1 growth medium. Of the 18 wells of H249 cells the mean control cell count on day 4 was $2.16 (\pm 0.82) \times 10^5$ cells while the mean of the group subjected to the pulsed field was $1.49 (\pm 0.81) \times 10^5$, a mean % reduction of 32%. Of the 16 wells of H146 cells, the mean control cell count on day 4 was $8.25 (\pm 3.46) \times 10^5$ cells, while the mean of the group subjected to the pulsed field was $5.42 (\pm 2.25) \, 10^5$ cells, a mean reduction of 34%. This study indicates that highly specific electromagnetic fields can inhibit the growth of small cell lines. It is likely that an improved inhibition can be attained using varying pulsed field parameters.

All of the cells used in the present Study and Studies 4–6 were obtained from the National Cancer Institute, Maryland, U.S.A.

Study 4

A study was carried out to examine the impact on cell growth of seven different cell lines incubated for 96 h. with continuous exposure to a low energy 27 MHz pulsed electromagnetic field under incubation conditions similar to those used in Study 3. One of the cell lines H249 was subsequently incubated for a further 96 h. Cells were plated in 96 well plates and an equal number of controls set up in parallel. The results are shown in Table 1.

TABLE 1

| Cell line | Mean % inhibition after exposure to pulsed radiofrequency |
|---|---|
| H146 (lung) | 34% |
| H249 (lung 4/7) | 32% |
| H249 (lung 8/7) | 52% |
| H125 (lung) | 34% |
| MCF7WT (breast) | 22% |
| OAW4 (ovary) | 12% |
| 234 (melanoma) | 41% |
| HL60 (polymorph) | 34% |

This study shows that pulsed radiofrequency inhibits several cell types and that the ability of such pulsed radiofrequency to inhibit different cell types varies considerably. Prolonging the exposure can result in a significant improvement in the % inhibition as attained in the case of cell line H249.

Study 5

A further Study was carried out to examine the impact on cell growth of four cell lines incubated for 96 h. with continuous exposure to a low energy 27 MHz pulsed electromagnetic field under incubation conditions similar to those used in Study 3 and as indicated in Table 2. The results are shown in Table 2.

TABLE 2

Inhibition of cell growth by pulsed electromagnetic frequencies (PEMF)

| Cell line | Number of wells | Number of cells plated | Controls ± S.D. × $10^5$ cells/well | Cells exposed to PEMF × $10^5$ cells/well | % inhibition |
|---|---|---|---|---|---|
| 234 (Melanoma) | 30 | $1 \times 10^5$ | 3.17 ± 1.20 | 1.86 ± 0.76 | 41 |
| 125 Adeno Carcinoma (skin 2°) | 30 | $2 \times 10^5$ | 47.7 ± 11.04 | 31.46 ± 7.7 | 34 |
| MCF 7WT (Breast) | 28 | $1 \times 10^5$ | 39.7 ± 12.62 | 26.75 ± 11.51 | 22 |
| OAW4 (Ovarian) | 31 | $1 \times 10^5$ | 3.04 ± 1.24 | 2.67 ± 0.85 | 12 |

Study 6

A study was carried out to determine the effect of pulsed radiofrequency (27 MHz) on four malignant cell lines after exposure to cisplatin for a period of 2 h. under the conditions indicated in Table 3. $1 \times 10^5$ cells were plated in each case. After the exposure to cisplatin the cells were divided into two groups. The first group was incubated for 96 h. with continuous exposure to the pulsed electromagnetic field under conditions similar to those used in Study 3. The second group served as controls in equal number. The results are shown in Table 3.

TABLE 3

Inhibitory effect of pulsed radiofrequency on malignant cell lines following exposure to cisplatin

| Cell line | Cisplatin concn | Number of wells | Mean of controls × $10^5$ cells/well | Mean of cells exposed to PEMF × $10^5$ cells/well | % inhibition |
|---|---|---|---|---|---|
| 234 (Melanoma) | 0.03 mg/ml | 24 | 0.69 | 0.398 | 42% |
| MCF7 Adr⁻ (Breast) | 0.3 mg/ml | 35 | 2.69 | 1.295 | 52% |
| 417 (Lung) | 0.3 mg/ml | 27 | 1.51 | 0.79 | 48% |
| MCF7WT (Breast) | 0.03 mg/ml | 24 | 7.15 | 3.95 | 45% |

A comparison of the results obtained for the cell line MCF7WT in Study 5 (22% inhibition) relative to the result obtained above (45% inhibition) would indicate that the use of PEMF serves to potentiate the effect of the chemotherapeutic agent.

What is claim:

1. A device for the controlled emission of electromagnetic radiation for use in medical and surgical conditions in humans and animals, which device comprises:

a substrate which is adapted to be contoured to and placed in intimate contact with an area of the body of said human or animal to be treated;

an electrical circuit which is integral and flexible with said substrate;

said electrical circuit including at least one inductance coil for the generation of electromagnetic radiation; and a power supply connected to said circuit, such that the electromagnetic radiation is generated at the site of application of the device.

2. A device according to claim 1, wherein the electromagnetic radiation emitted by the device is continuous.

3. A device according to claim 1, wherein the electromagnetic radiation emitted by the device is pulsed.

4. A device according to claim 3, wherein the electrical circuit includes a pulse generating circuit and a pulse shaping network.

5. A device according to claim 1, wherein the electromagnetic radiation emitted is of a single waveform.

6. A device according to claim 5, wherein the waveform is sinusoidal.

7. A device according to claim 1, wherein the electromagnetic radiation emitted comprises a plurality of waveforms.

8. A device according to claim 1, wherein the electromagentic radiation is emitted as a basic waveform which is shaped to produce harmonics thereof.

9. A device according to claim 1, wherein the electromagnetic radiation produced has a nominal frequency in the range 20–30 MHz.

10. A device according to claim 1, wherein the electromagnetic radiation produced has a nominal frequency of 27 MHz.

11. A device according to claim 1, which generates mean power in the range 1 to 3 milliwatts per $cm^2$ at the surface of the area of the body to be treated.

12. A device according to claim 1, which includes a pair of flat rectangular helical inductance coils.

13. A device according to claim 1, wherein the substrate is affixed to a pad of a cushioning material and is housed in a sleeve for ready application to the body of a human or animal to be treated.

14. A device according to any claim 1, wherein the power supply consists of one or more batteries.

15. A device according to claim 1, wherein the power supply is integral with said substrate.

16. A device according to claim 1, which is in the form of a cervical collar for use in the treatment of acute or chronic neck pain.

17. A device according to claim 1, which is in the form of a cervical collar for use in the treatment and alleviation of symptoms in symptomatic cervical spondylosis, whiplash injuries and persistent neck pain.

18. A device according to claim 1, wherein the electromagnetic radiation emitted by the device is pulsed and the pulse burst width is of the order of 50–70 μsec.

19. A device according to claim 1, wherein the electromagnetic radiation emitted by the device is pulsed and the pulse burst width is of the order of 60 μsec.

20. A device according to claim 1, wherein the electromagnetic radiation has a repetition frequency of the order of 400–500 cycles per second.

21. A device according to claim 1, wherein the electromagnetic radiation has a repetition frequency of the order of 450 cycles per second.

22. A device according to claim 1, wherein the electromagentic radiation emitted by the device is pulsed and the pulse burst width is of the order of 250–350 μsec.

23. A device according to claim 1, wherein the pulse burst width is of the order of 300 μsec.

24. A device according to claim 1, wherein the electromagnetic radiation has repetition frequency of the order of 200–400 cycles per second.

25. A device according to claim 1 wherein the electromagnetic radiation has a repetition frequency of the order of 333 cycles per second.

26. A device according to claim 1 in combination with a chemotherapeutic agent for use in the treatment of malignancies, such use being simultaneous, separate or sequential.

27. A device according to claim 26, wherein the chemotherapeutic agent is metallo-organic compound.

28. A device according to claim 26, wherein the chemotherapeutic agent is a platinum compound.

29. A device according to claim 26, wherein the chemotherapeutic agent is cisplatin.

* * * * *